United States Patent [19]

Tanaka et al.

[11] Patent Number: 5,202,570
[45] Date of Patent: Apr. 13, 1993

[54] GAS DETECTION DEVICE

[75] Inventors: Hiroaki Tanaka; Masayuki Matsuura; Hideo Tai; Kiyoji Uehara, all of Tokyo, Japan

[73] Assignee: Tokyo Gas Co., Ltd., Tokyo, Japan

[21] Appl. No.: 673,886

[22] Filed: Mar. 22, 1991

[30] Foreign Application Priority Data

Mar. 27, 1990 [JP] Japan .................................. 2-78498
Jul. 10, 1990 [JP] Japan ................................ 2-183667
Sep. 18, 1990 [JP] Japan ................................ 2-246331

[51] Int. Cl.⁵ ........................ G01N 21/59; G01J 3/42
[52] U.S. Cl. .................................... 250/575; 250/205; 250/338.5; 250/339; 250/573
[58] Field of Search .................. 356/435, 436, 437; 250/575, 573, 205, 338.5, 339, 343, 341

[56] References Cited

U.S. PATENT DOCUMENTS

| | | | |
|---|---|---|---|
| 4,017,186 | 4/1977 | Shofner et al. | 356/342 |
| 4,410,273 | 10/1983 | Mantz et al. | 250/339 X |
| 4,701,607 | 10/1987 | El-Hanany et al. | 250/205 |
| 4,849,637 | 7/1989 | Cerff et al. | 250/343 X |
| 4,853,543 | 8/1989 | Ozdemir | |
| 4,927,485 | 5/1990 | Cheng et al. | 356/357 X |
| 4,998,256 | 3/1991 | Ohshima et al. | 372/43 X |
| 5,015,099 | 5/1991 | Nagai et al. | 250/338.5 |
| 5,026,991 | 6/1991 | Goldstein et al. | 250/343 |
| 5,047,639 | 9/1991 | Wong | 250/343 X |

FOREIGN PATENT DOCUMENTS

| | | |
|---|---|---|
| 0195179 | 9/1986 | European Pat. Off. |
| 0263931 | 4/1988 | European Pat. Off. |
| A-58-081353 | 5/1983 | Japan |
| 63-9843 | 1/1988 | Japan ........................ 356/437 |
| 89/03028 | 4/1989 | World Int. Prop. O. ........ 356/437 |

OTHER PUBLICATIONS

R. O. Miles, et al.; "Feedback-Induced Line Broadening in CW Channel-Substrate Planar Laser Diodes", in: Appl. Phys. Lett. 37(11), Dec. 1, 1980; pp. 990-992.

Kiyoji Uehara, et al.; "Remote Detection of Methane with a 1.66-$\mu$m Diode Laser"; in: Applied Optics; vol. 31, No. 6; Feb. 20, 1992; pp. 809-814.

Claus Weitkamp; "Calibration of Diode-Laser Second-Derivative Modulation Spectrometry with a Reference Cell", in: Applied Optics, vol. 23, No. 1; Jan. 1, 1984; pp. 83-86.

Patent Abstracts of Japan, vol. 7, No. 174 (E-190), Aug. 2, 1983.

Primary Examiner—Constantine Hannaher
Assistant Examiner—Edward J. Glick
Attorney, Agent, or Firm—Townsend and Townsend

[57] ABSTRACT

A gas detection device employs a tunable wavelength laser, modulated about an absorption line of a gas to be detected. By measuring the ratio of the fundamental to the second harmonic of the modulation frequency, the detection is independent of the optical path length. This permits an aimable device in which a laser beam is directed toward a remote surface, reflected thereby, and the reflected beam focused upon a detector. The presence of the gas to be detected in the space between the device and the reflective surface is thereby determined.

1 Claim, 10 Drawing Sheets

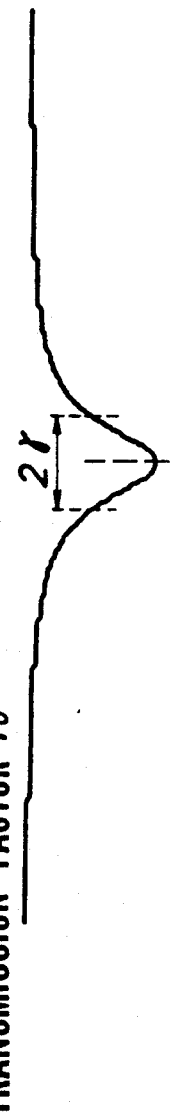
FIG. 2A  TRANSMISSION FACTOR $T_0$
FIG. 2B  FIRST DERIVATIVE $T_0'$
FIG. 2C  SECOND DERIVATIVE $T_0''$

WAVE LENGTH

INTENSITY OF LASER BEAM

1 MINUTE

GAS DETECTION DEVICE

BACKGROUND OF THE INVENT

1. Field of the Invention

The present invention relates to a gas detection device using a semiconductor laser, and, in particular, to a gas detection device suitable for remote quantitative gas concentration measurements.

2. Description of the Prior Art

Methods of detecting the presence of a gas, utilizing the characteristics of gases to absorb laser beams of specific wavelengths, are commonly known. Sensing technology based on this principle is widely used in industrial measurements, pollution monitoring, and the like. For example, methane strongly absorbs the 3,392 $\mu$m emission of the He-Ne laser, but absorbs only slightly the 3,391 $\mu$m emission of the same laser. Accordingly, it is possible to detect the presence of methane with good sensitivity from the difference between the strengths of the transmitted light when laser beams of two wavelengths with equal intensity strike the gas being probed. Because methane is the main constituent of city gas, it is possible to detect leaks of city gas by detecting the methane gas.

A methane leak sensor of this type is disclosed in U.S. Pat. No. 4,489,239. However, this sensor requires two lasers, two choppers, and two lock-in amplifiers, which makes the device voluminous. At the same time, this U.S. patent also proposes a laser device which oscillates at two wavelengths simultaneously and thus eliminates this drawback. However, some problems still remain, such as the difficulty in maintaining equal output powers at the two wavelengths.

Another known method uses one mechanical chopper to equalize the output powers at the two wavelengths from two separate lasers. However, a methane detection system of this type needs many mirrors and beam splitters, making the optical system very complicated. Therefore, optical alignment is troublesome and the laser power loss is large. Furthermore, the signal processing is complicated, and high frequency modulation to attain high signal-to-noise ratio (S/N) cannot be accomplished because the mechanical chopper is used.

Accordingly, the inventors of the present invention, in Japanese Laid Open Patent Application 62-290190, proposed a novel two-frequency oscillation gas laser device which eliminates the drawbacks of the laser device used in the above-mentioned conventional gas detection systems. This two-frequency gas laser device oscillates alternately at two different wavelengths. Feedback is provided to adjust the cavity length so that the intensities of the two components are equal. Gas can be detected with this concise structure in which only one laser oscillator is used.

However, this two-frequency gas laser device has some drawbacks, too. Firstly, the instability of the laser cavity due to thermal expansion and mechanical vibrations disturbs the feedback control of the laser. Therefore, a high sensitivity gas detection is difficult to achieve. This drawback becomes a more severe problem when a portable device used in the field is considered. Secondly, a rather high electric power is necessary to produce a high voltage to operate the gas laser device. This is also a problem for a portable device.

SUMMARY OF THE INVENTION

The first object of the present invention is to provide, with due consideration of the drawbacks of the conventional devices, a highly sensitive gas detection device using a semiconductor laser modulated at a high frequency.

The second object of the present invention is to provide a portable gas detection device using a small laser transmitter-receiver unit which emits a laser beam toward a reflecting target and collects the light reflected by the target.

The first object is achieved in the present invention by the provision of a structure wherein the driving current of a semiconductor laser is modulated at a high frequency $\omega$ and the wavelength of the semiconductor laser is stabilized at the center or other position of an absorption line of the probed chemical species. This laser beam is then transmitted through the probed atmosphere and received by a detector. The gas concentration is measured from the fundamental ($\omega$) or the second harmonic ($2\omega$) components in the detected laser beam.

The second object is achieved in the present invention by the provision of a laser transmitter-receiver unit comprising: a laser transmitter which emits a collimated beam of the laser light whose wavelength is stabilized by using a reference gas cell; and a light receiver which consists of a focusing lens and a detector collinear with the laser transmitter.

BRIEF DESCRIPTION OF THE ACCOMPANYING DRAWINGS

These and other objects, features, and advantages of the present invention will become more apparent from the following description of the preferred embodiments taken in conjunction with the accompanying drawings, in which:

FIG. 2A is a graph of a transmittance vs. frequency based on an absorption line.

FIG. 2B is the first derivative signal of the absorption line shown in FIG. 2A.

FIG. 2C is the second derivative signal of the absorption line shown in FIG. 2A.

DETAILED DESCRIPTION OF THE PREFERRED EMBODIMENTS

First, the basic characteristics of a modulated semiconductor laser is outlined in (1) and (2), because they are essential to an understanding of the invention. Then, in (3), the method of gas detection will be described in detail.

(1) Frequency Modulation

One method of improving measurement sensitivity in spectrometry is the technique known as frequency modulation. The frequency of light can be modulated by many different means. When the modulated light passes through a target absorbent gas, the output signal from a detector which receives the light has the fundamental component of the modulation frequency and its higher harmonic components. The fundamental component and the second harmonic component detected by phase-sensitive detection correspond, respectively, to the first derivative and the second derivative of the profile of the absorption line. Here, phase sensitivity detection is defined as extracting the component of the signal with a specific frequency and phase and measuring its amplitude. A reference signal of the same frequency as the modulation frequency or its harmonics and a device called a lock-in amplifier are used. With this technique, the detection of extremely weak absorption is possible.

Now, the characteristics of the signal obtained by the frequency modulation method will be explained in an example where methane is detected by using a semiconductor laser as the light source.

Figure 1A:
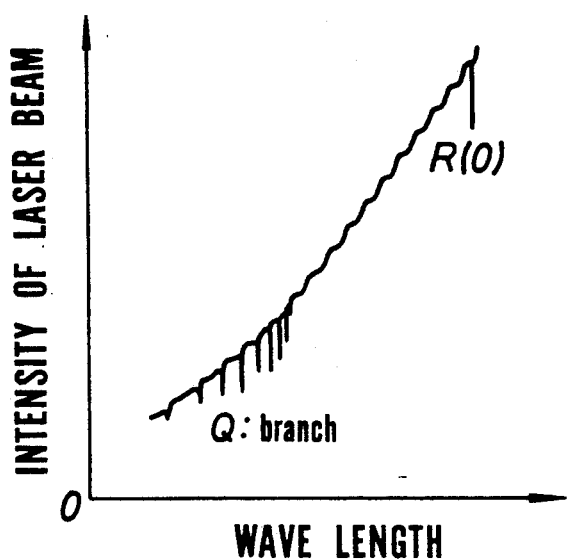
FIG. 1A is a graph of the absorption spectrum of methane around 1.665 $\mu$m.
Figure 1B:
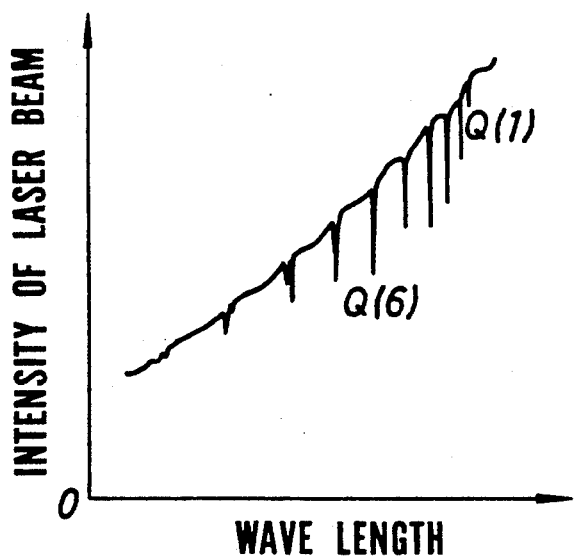
FIG. 1B is an enlarged view of a part of FIG. 1A.

As is commonly known, the transmittance T of a laser beam can be expressed as:

$$T = \exp(-\alpha c l) \qquad (1)$$

where c is the concentration of methane (partial pressure), l is the optical path length, and $\alpha$ is the absorption coefficient of methane. At atmospheric pressure each absorption line has a profile given by.

$$\alpha = \frac{\gamma^2 \alpha_o}{(\Omega - \omega_m)^2 + \gamma^2} \qquad (2)$$

where
$\Omega$: frequency of light
$\omega_m$: center frequency of absorption line
$\alpha_0, \gamma$: constants FIG. 1A is the absorption spectrum of the $2\nu_3$ band of methane around 1.665 μm, observed by using a semiconductor laser. FIG. 1B is an enlarged view of a part of FIG. 1A. Basically, each line has an absorption profile as shown in FIG. 2A and expressed by equation (2). In the case of the Q(6) line, the center frequency $\omega_m$ is about $1.800 \times 10^{14}$ Hz (6002.6 cm$^{-1}$ in wave number). Here, $2\gamma$ represents the half width of the absorption line, which for methane at atmospheric pressure is about $4 \times 10^9$ Hz (0.13 cm$^{-1}$). $\alpha_0$ represents the absorption coefficient at the center of the absorption line. The value of $\alpha_0$ for the Q(6) line at one atmosphere of pressure is 40 m$^{-1}$atm$^{-1}$.

When $\alpha c l < 1$, equations (1) and (2) give $$T = 1 - \alpha c l = 1 - \frac{\gamma^2 \alpha_o c l}{(\Omega - \omega_m)^2 + \gamma^2} \qquad (3)$$

as a close approximation.

The oscillation frequency $\Omega$ of the semiconductor laser depends on both the temperature and the drive current. When the temperature is fixed and the drive current is modulated at the frequency $\omega$, the oscillation frequency $\Omega$ is modulated at the frequency $\omega$ as expressed by.

$$\Omega = \Omega_o + \Delta\Omega \cos \omega t \qquad (4)$$

where
$\Omega_0$: center oscillation frequency
$\Delta\Omega$: modulation amplitude
$\omega$: modulation frequency By substituting equation (4) into equation (3) and expanding T with respect to $\Delta\Omega$, we obtain $$T = T_o + \frac{(\Delta\Omega)^2}{4} T_o'' + \Delta\Omega T_o' \cos(\omega t) + \frac{(\Delta\Omega)^2}{4} T_o'' \cos(2\omega t) \qquad (5)$$

Here, $T_o$, $T_o'$, and $T_o''$ are respectively the transmittance T, its first derivative $dT/d\Omega$, and the second derivative $d^2T/d\Omega^2$ at $\Omega = \Omega_o$. Their explicit expressions are as follows:

$$T_o = 1 - \frac{\gamma^2 \alpha_o c l}{(\Omega_o - \omega_m)^2 + \gamma^2} \qquad (6)$$

$$T_o' = \frac{2(\Omega_o - \omega_m)\gamma^2 \alpha_o c l}{[(\Omega_o - \omega_m)^2 + \gamma^2]^2} \qquad (7)$$

$$T_o'' = \frac{-2[3(\Omega_o - \omega_m)^2 - \gamma^2]\gamma^2 \alpha_o c l}{[(\Omega_o - \omega_m)^2 + \gamma^2]^3} \qquad (8)$$

The curves of $T_o$, $T_o'$, and $T_o''$ as functions of $\Omega_0$ are shown in FIGS. 2A, 2B, and 2C, respectively. Note that the coefficients of the cos ($\omega t$) and cos ($2\omega t$) components in equation (5) are proportional to $T_o'$, and $T_o''$, respectively.

At the line center, i.e. $\Omega_o = \omega_m$, $T_o$ becomes minimum, $T_o'$ becomes 0, and $T_o''$ becomes maximum. Their values are:

$$T_o(\Omega_o = \omega_m) = 1 - \alpha_o c l \qquad (9)$$

$$T_o'(\Omega_o = \omega_m) = 0 \qquad (10)$$

$$T_o''(\Omega_o = \omega_m) = 2\alpha_o c l / \gamma^2 \qquad (11)$$

When $T_o'' = 0$, on the other hand, $T_o'$ becomes maximum or minimum. This happens when $$\Omega_o = \omega_m \pm \gamma/\sqrt{3} \qquad (12)$$

(2) Intensity Modulation

As mentioned above, the frequency modulation of a semiconductor laser is accomplished by modulating the drive current. However, when the drive current of a semiconductor is modulated, the output power of the laser is also subjected to modulation at the same time. This intensity modulation gives an additional phase sensitive signal which is unrelated to absorption as shown in the following.

In addition to frequency modulation expressed by equation (4), the laser suffers modulation in intensity I given by $$I = I_o + \Delta I \cos(\omega t + \phi) \quad (13)$$

where
$I_o$: mean intensity of laser output
and $\Delta I$: intensity modulation amplitude
Here, $\phi$ is the phase difference between the intensity modulation and the frequency modulation.

The intensity P of the laser beam after passing through methane is in proportion to the intensity I and the transmittance T, so that:

$$P = A \cdot I \cdot T \quad (14)$$

Here, the coefficient A is a constant which depends on various factors. In a system which utilizes an optional reflecting surface as a target, A depends on the distance to the target, its reflectance, etc.

When equation (5) and equation (13) are substituted into equation (14), we obtain.

$$P = A[I_o + \Delta I \cos(\omega t + \phi)] \cdot \quad (15)$$
$$\left[ C_o + \Delta\Omega T_o' \cos(\omega t) + \frac{(\Delta\Omega)^2}{4} T_o'' \cos(2\omega t) \right]$$

where $$C_o = T_o + \frac{(\Delta\Omega)^2}{4} T_o'' \quad (16)$$

By expanding equation (15) and neglecting the higher-order terms we see that the portion of P changing at the frequency $\omega$ consists of two terms:

$$A\, C_o\, \Delta I \cos(\omega t + \phi) + A\, I_o\, \Delta\Omega T_o' \cos\omega t \quad (17)$$

The two terms in expression (17) have different phases. Accordingly, in phase sensitivity detection, selection of the phase of the reference signal changes the contributions of the two terms.

First, at the phase of the reference signal where the contribution of the first term in equation (17) is a maximum, the phase-sensitive-detected signal at $\omega$ becomes $$P(\omega) = A[\Delta I\, C_o + I_o \Delta\Omega T_o' \cos\phi] \quad (18)$$

The second term in equation (18) is the contribution from the second term in equation (17). Here, we used the identity $$\cos\omega t = \cos(\omega t + \phi - \phi) \quad (19)$$
$$= \cos\phi\cos(\omega t + \phi) + \sin\phi\sin(\omega t + \phi)$$

On the other hand, at the phase where the contribution of the first term in equation (17) vanishes $P(\omega)$ becomes $$P(\omega) = A\, I_o \Delta\Omega T_o' \sin\phi \quad (20)$$

Note that $\Delta I$ does not appear in equation (20), i.e., the effect of intensity modulation is absent.

Figure 3:
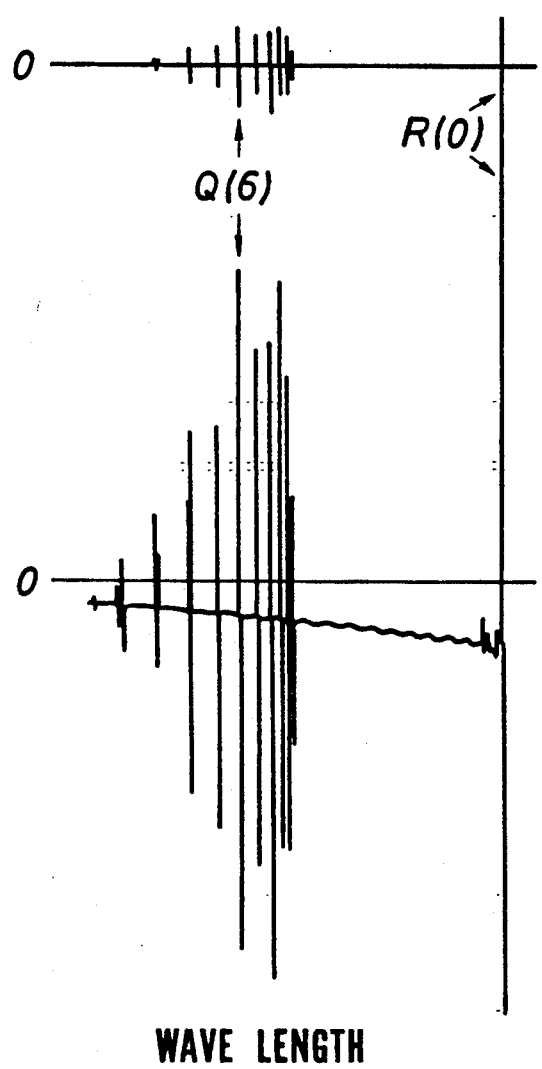
FIG. 3 shows the first derivative signals of the methane absorption lines observed at two different phases in phase sensitive detection.

The upper trace and the lower trace in FIG. 3 show the fundamental frequency detection signals at the two phases where the intensity modulation signal becomes the minimum and the maximum, respectively, corresponding to equations (20) and (18).

(3) Method of Gas Detection

Now, the method for detection of a gas is explained, based on the foregoing preliminary considerations.

The absorption of methane is detected by the phase-sensitive detection of the transmitted beam intensity at the fundamental or second harmonics of the modulation frequency $\omega$. In order to obtain the maximum signal intensity it is necessary to stabilize the center frequency of the laser $\Omega_o$ at an appropriate position on the absorption line. This stabilization can be implemented by passing a part of the laser beam through a reference cell filled with methane and detecting the intensity variation of the transmitted beam.

If the methane gas is to be detected by phase sensitive detection at the fundamental frequency, the center frequency $\Omega_o$ must be stabilized at the frequency given by equation (12) where $T_o'$ is maximum and $T_o''$ is 0. Therefore, the phase sensitive detection at the second harmonics is used to control the laser frequency so that $T_o''$ becomes 0.

In the other case where the methane is detected by phase sensitive detection at the second harmonics, the center frequency $\Omega_o$ must be stabilized at the center of the absorption line. In this case, the fundamental frequency signal $P(\omega)$, given by equation (20) obtained from the beam passed through the reference cell is used to control the laser frequency.

In either case, the laser frequency can be stabilized by the feedback control of the temperature or the drive current.

Either of the two methods can be utilized in practice, but in the following embodiments the frequency is stabilized at the center of the absorption line by the fundamental frequency signal and methane is detected by the second harmonic signal.

After the laser frequency is stabilized at the center of the methane absorption line, the $2\omega$ component in the beam intensity, after it has passed through the probed atmosphere, is detected by phase sensitivity detection. The detected signal, $P(2\omega)$, becomes from equations (15) and (11):

$$P(2\omega) = AI_o(\Delta\Omega)^2 T_o''/4 \quad (21)$$
$$= AI_o(\Delta\Omega)^2 \cdot \alpha_o c l / 2\gamma^2$$

$P(2\omega)$ is proportional to the product cl of the methane concentration c and the optical path length l. Therefore, if the coefficient A is a constant, the quantitative measurement of methane can be made directly from $P(2\omega)$. However, under the measurement conditions when A is variable, a quantitative measurement cannot be made directly. In this case, the $\omega$ component becomes useful. The signal $P(\omega)$ at $\Omega_o = \omega_m$ becomes, from equations (18) and (8):

$$P(\omega) = A\Delta I C_o \qquad (22)$$
$$= A\Delta I$$

Accordingly, the ratio R of $P(2\omega)$ to $P(\omega)$ is:

$$R = P(2\omega)/P(\omega) \qquad (23)$$
$$= \frac{I_o(\Delta\Omega)^2 a_o}{2\Delta I \gamma^2} \cdot cl$$

It should be noted that the unknown constant A does not appear in R. Therefore, the product cl of the methane concentration c and the optical path length l can be measured from R independent of the unknown factor A.

Figure 4A:
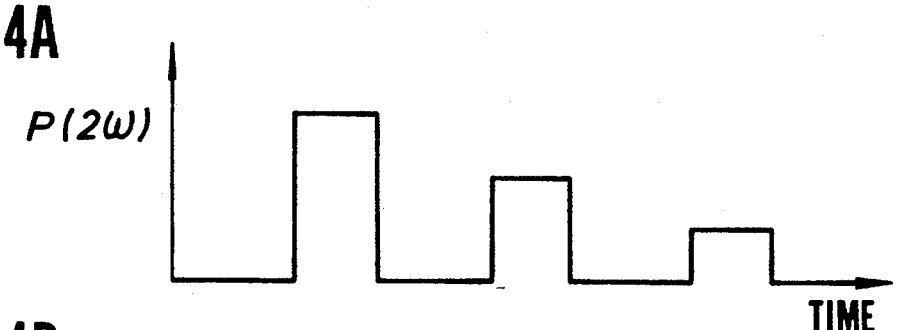
FIGS. 4A, 4B, 4C are the phase sensitive detected signals P($2\omega$) and P($\omega$), and their ratio R showing the usefulness of the present invention.
Figure 4B:
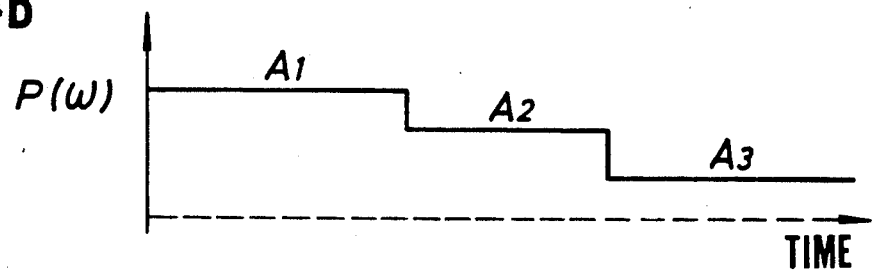
Figure 4C:
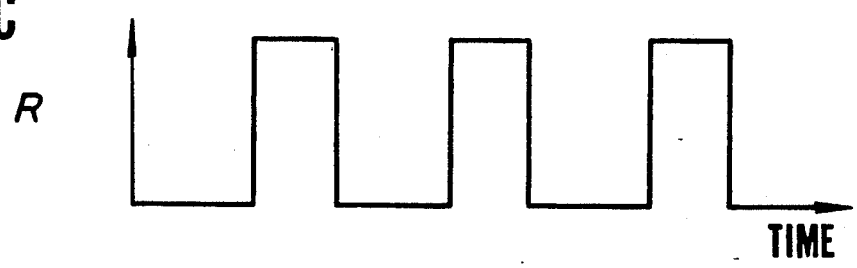

FIGS. 4A, 4B, 4C show the changes in the signals $P(2\omega)$ and $P(\omega)$ and their ratio R, when the constant A takes three values $A_1$, $A_2$, and $A_3$. While $P(2\omega)$ and $P(\omega)$ change, the ratio R remains constant. This means that methane can be detected quantitatively by simultaneous detection of the fundamental signal $P(\omega)$ and the second harmonic signal $P(2\omega)$.

In this manner, the concentration of a the probed gas can be measured by means of the present invention regardless of the unknown factor A which depends on the distance to the reflection target, its reflectance, etc.

Figure 5:
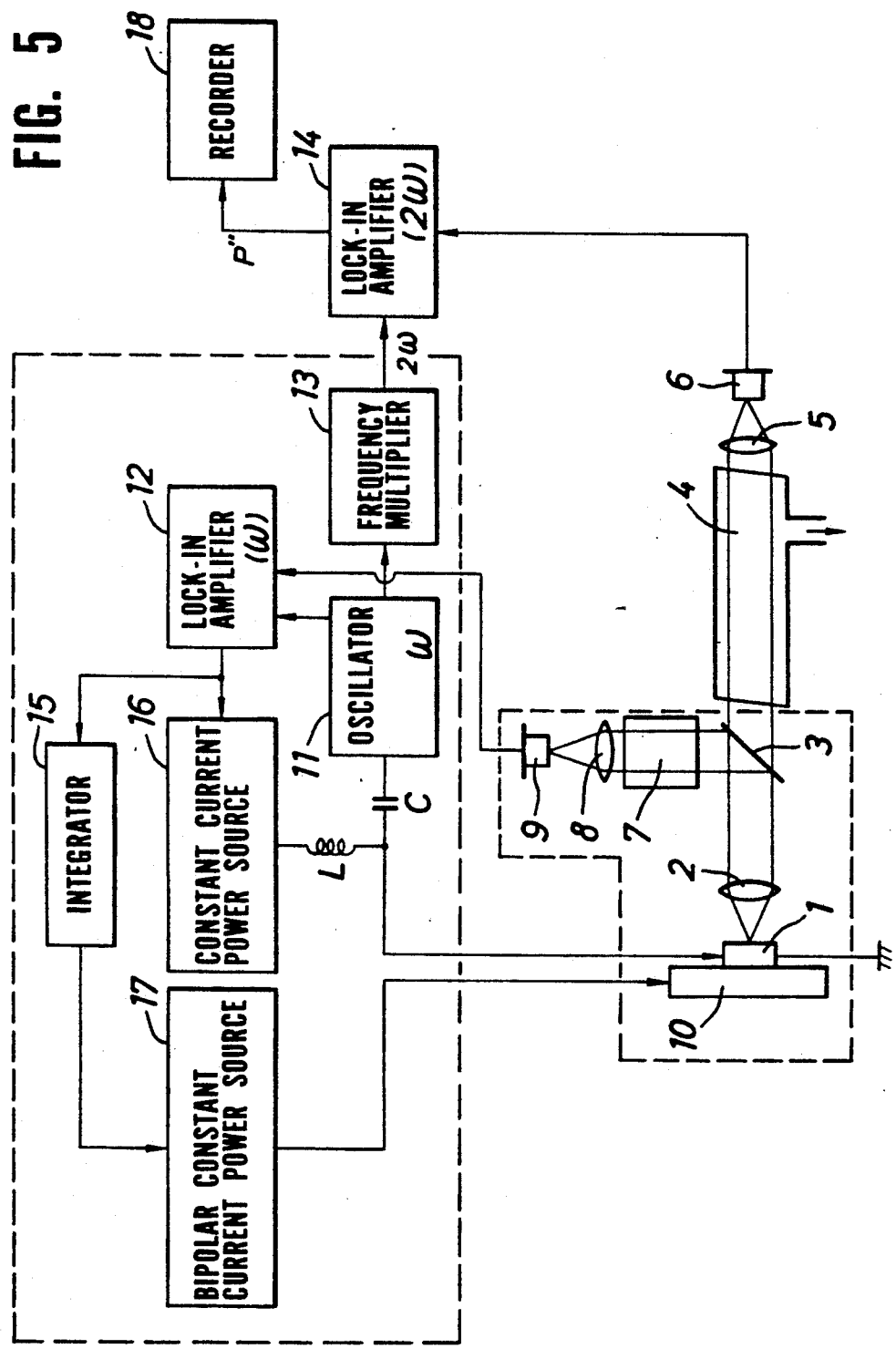
FIG. 5 is a block diagram of an embodiment of the gas detection device of the present invention.

FIG. 5 is a block diagram of an embodiment of the gas detection device of the present invention which is capable of quantitative measurement of methane.

Now referring to FIG. 5, the gas detection device of the present invention comprises a semiconductor laser 1; a collimator lens 2 for converting a laser beam generated by the semiconductor laser 1 into a parallel beam; a beam splitter 3 for splitting the laser beam; a test cell 4 containing the probed gas; a condensing lens 5 which condenses the laser beam transmitted through the test cell 4; a light detector 6 such as a PIN photodiode or the like which detects the intensity of the laser beam; a reference cell 7 containing methane gas; a condensing lens 8 which condenses the laser beam passing through the reference cell 7; a light detector 9 such as a PIN photodiode or the like which detects the intensity of the laser beam transmitted through the reference cell 7; a Peltier element 10 for controlling the temperature of the semiconductor laser 1; an oscillator 11 for modulating the laser drive current at a frequency $\omega$; a lock-in amplifier 12 which is synchronized with the frequency $\omega$ and detects the $\omega$ component of the signal from the light detector 9; a frequency multiplier 13 which doubles the frequency $\omega$ to $2\omega$; a lock-in amplifier 14 which is synchronized at the frequency $2\omega$ and detects the $2\omega$ component of the signal from the light detector 6; an integrator 15 which integrates the output of the lock-in amplifier 12; a constant-current power source 16 which drives the laser at a current depending on the output of the lock-in amplifier 12; a bipolar constant current power source 17 which supplies a constant current of either positive or negative polarity depending on the output of the integrator 15; and a recorder 18 which records the output $P(2\omega)$ of the lock-in amplifier 14.

The operation of this gas detection device will now be explained.

In general, a higher modulation frequency results in a higher signal-to-noise ratio (S/N ratio).

Therefore 25 MHz is selected as the oscillation frequency $\omega$ of the oscillator 11. A sinusoidal current of 25 MHz from the oscillator 11 is added to the constant current from the constant-current power source 16 via a capacitor C, to modulate the semiconductor laser 1. An inductance L is connected to the output side of the constant-current power source 16 to avoid any effects from the output of the oscillator 11.

The frequency multiplier 13 doubles the frequency $\omega$ (25 MHz) of the reference signal output of the oscillator 11, to provide a reference signal of 50 MHz.

Figure 7:
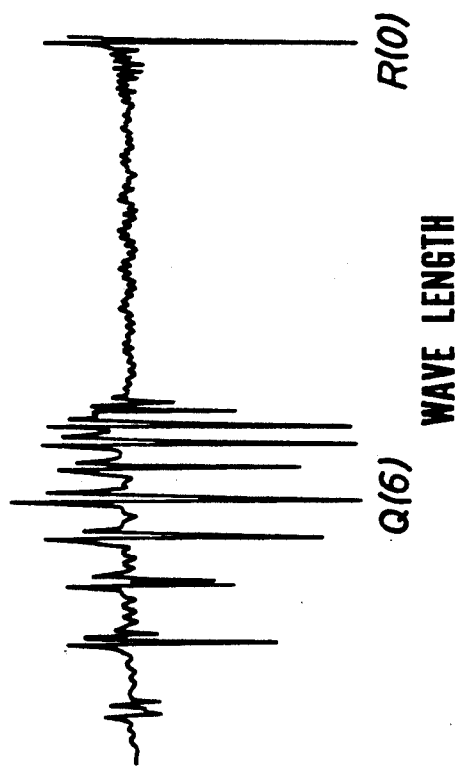
FIG. 7 shows the second derivative signals of the methane absorption lines.

First, nitrogen gas at one atmosphere pressure containing 1% methane is filled into the test cell 4. The second harmonic signal as shown in FIG. 7 is obtained when the frequency of the semiconductor laser 1 is swept by changing the temperature. Because the Q(6) line gives the largest signal in the measured range, the Q(6) line is seen to be the most suitable for methane detection. In order to stabilize the oscillation frequency of the semiconductor laser 1 at the center of the Q(6) line, the reference cell 7 is filled with a methane-nitrogen mixture at a total pressure of one atmosphere. The output signal from the detector 9 is fed into the lock-in amplifier 12. The lock-in detected signal $P(\omega)$, after it is integrated by the integrator 15, is treated as an error signal which changes the output current of the bipolar constant-current power source 17 and thus controls the temperature of the semiconductor laser 1. At the same time, the constant current power source 16 controls the drive current of the semiconductor laser 1 depending on the output from the lock-in amplifier 12. In this manner, the oscillation frequency of the semiconductor laser 1 is stabilized at the center of the Q(6) line. The output signal $P(2\omega)$ of the lock-in amplifier 14 is in proportion to the product cl of the methane gas in the test cell 4. Once the signal is calibrated by a test gas of known concentration, the methane concentration can be measured from $P(2\omega)$. $P(2\omega)$ is recorded in the recorder 18.

Figure 8:
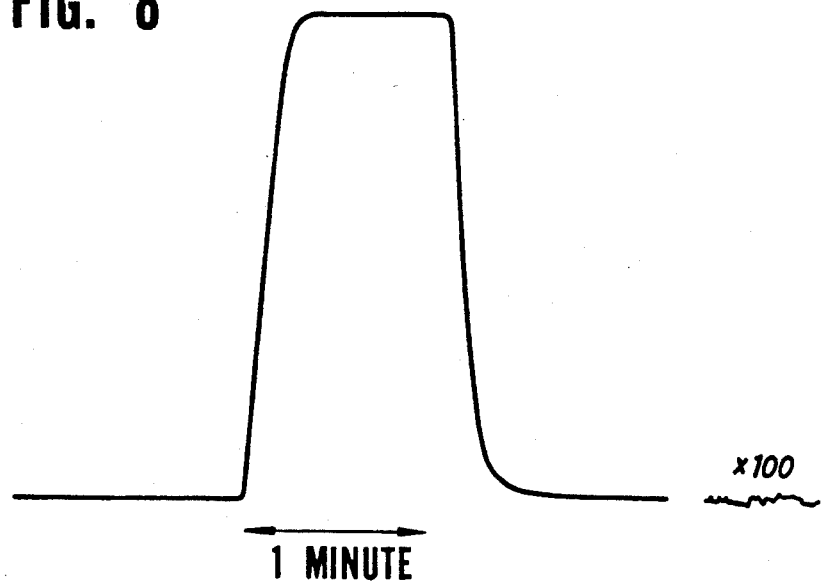
FIG. 8 is a methane detection signal by second harmonic detection.

FIG. 8 shows the second harmonic signal obtained when a methane-nitrogen mixture at one atmosphere containing 1% methane was introduced into the test cell 4, of 50 cm long. The noise level magnified 100 times is shown on the right side of this drawing. In FIG. 8 the S/N ratio is about 4000. If the detection limit corresponds to a S/N ratio=1, the minimum detectable product cl of the methane concentration c and the optical path length l is calculated to be 1.3 ppm·m. If a multiple reflection cell of 100 m path length is used as the test cell 4, low concentration methane down to 100 ppb can be detected.

Figure 6:
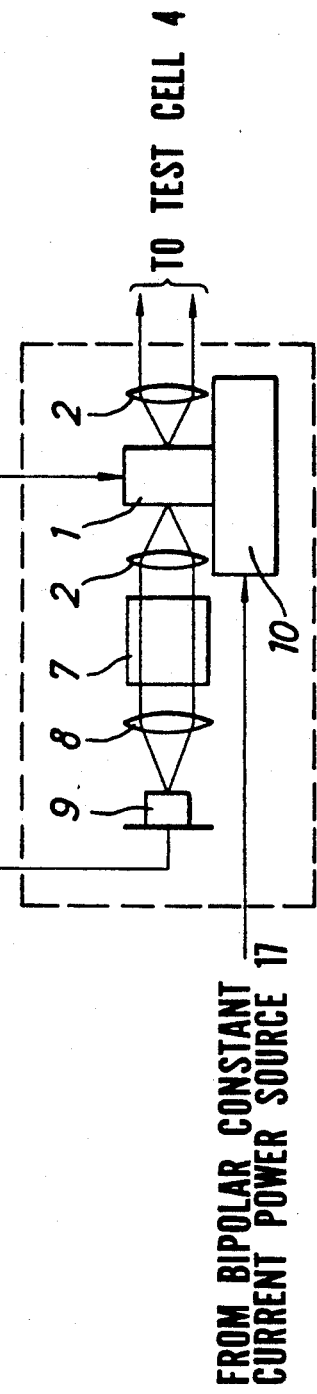
FIG. 6 is a block diagram of a modification of a part of the embodiment of the gas detection device shown in FIG. 5.

It is known that a semiconductor laser emits a laser beam in both the forward and backward directions. In view of this, the optical unit comprising the semiconductor laser 1, the collimator lens 2, the beam splitter 3, the reference cell 7, the condensing lens 8, the light detector 9, and the Peltier element 10, which is shown in the lower portion of FIG. 5 enclosed by a dashed line, can be modified as illustrated in FIG. 6 to provide an optical unit comprising the semiconductor laser 1, a pair of collimator lenses 2, the reference cell 7, the condensing lens 8, the light detector 9, and the Peltier element 10.

Figure 9:
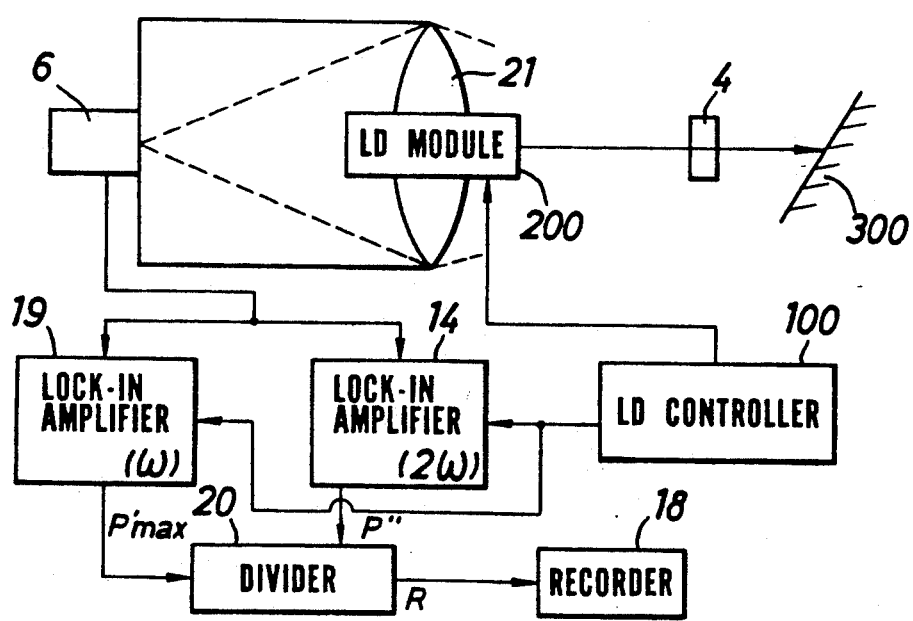
FIG. 9 is a block diagram of another embodiment of the gas detection device of the present invention.

FIG. 9 illustrates another embodiment of the gas detection device of the present invention for remote quantitative measurement of methane, which utilizes an arbitrary reflecting surface. Same numerals as in FIG. 5 are used in FIG. 9.

In this embodiment shown in FIG. 9, the laser beam first passes through the probed area and then is reflected from the reflecting surface. The reflected light again passes through the area and is focused on a detector.

The main structural elements of this embodiment are almost identical to those of the embodiment shown in FIG. 5. However, an LD controller 100 comprises the oscillator 11, the lock-in amplifier 12, the frequency multiplier 13, the integrator 15, the constant current power source 16, and the bipolar constant current power source 17 of FIG. 5. A laser transmitter 200 comprises as FIG. 6 the semiconductor laser 1, the collimator lens 2, the reference cell 7, the condensing lens 8, the light detector 9, and the Peltier element 10.

The points of difference in configuration between this embodiment in FIG. 9 and the embodiment illustrated in FIG. 5 are as follows. A large-aperture condensing lens 21 is used for collecting the laser light which passes through the test cell 4 and reflects from the reflecting surface 300. Also provided are an additional lock-in amplifier 19 which detects the fundamental signal $P(\omega)$, from the light detector 6, as well as a divider 20 which divides the output $P(2\omega)$ of the lock-in amplifier 14 by the output $P(\omega)$ of the lock-in amplifier 19 to obtain the ratio $R = P(2\omega)/P(\omega)$. The output R of the divider 20 is recorded in the recorder 18.

The operation of this embodiment is essentially the same as the operation of the embodiment shown in FIG. 5, but, as can be understood from the above-mentioned equation (23), the ratio R does not depend on the unknown factor A. Therefore, the product cl of the concentration and the optical path length can be measured regardless of the reflection conditions.

This embodiment can be utilized as a portable gas detection device because the laser transmitter and the receiver are assembled into a unit. The laser beam can be directed to any reflecting target.

Both above-mentioned embodiments use the fundamental frequency signal to stabilize the oscillation frequency of the semiconductor laser, and they detect the gas by the second harmonic signal. However, the converse is possible, i.e., the second harmonic signal may be used to stabilize the oscillation frequency of the semiconductor laser, and the fundamental frequency signal may be used to detect the gas. In this case, the lock-in amplifier 12 must be synchronized at the frequency $2\omega$ and the lock-in amplifier 14 at the frequency $\omega$.

Figure 10:
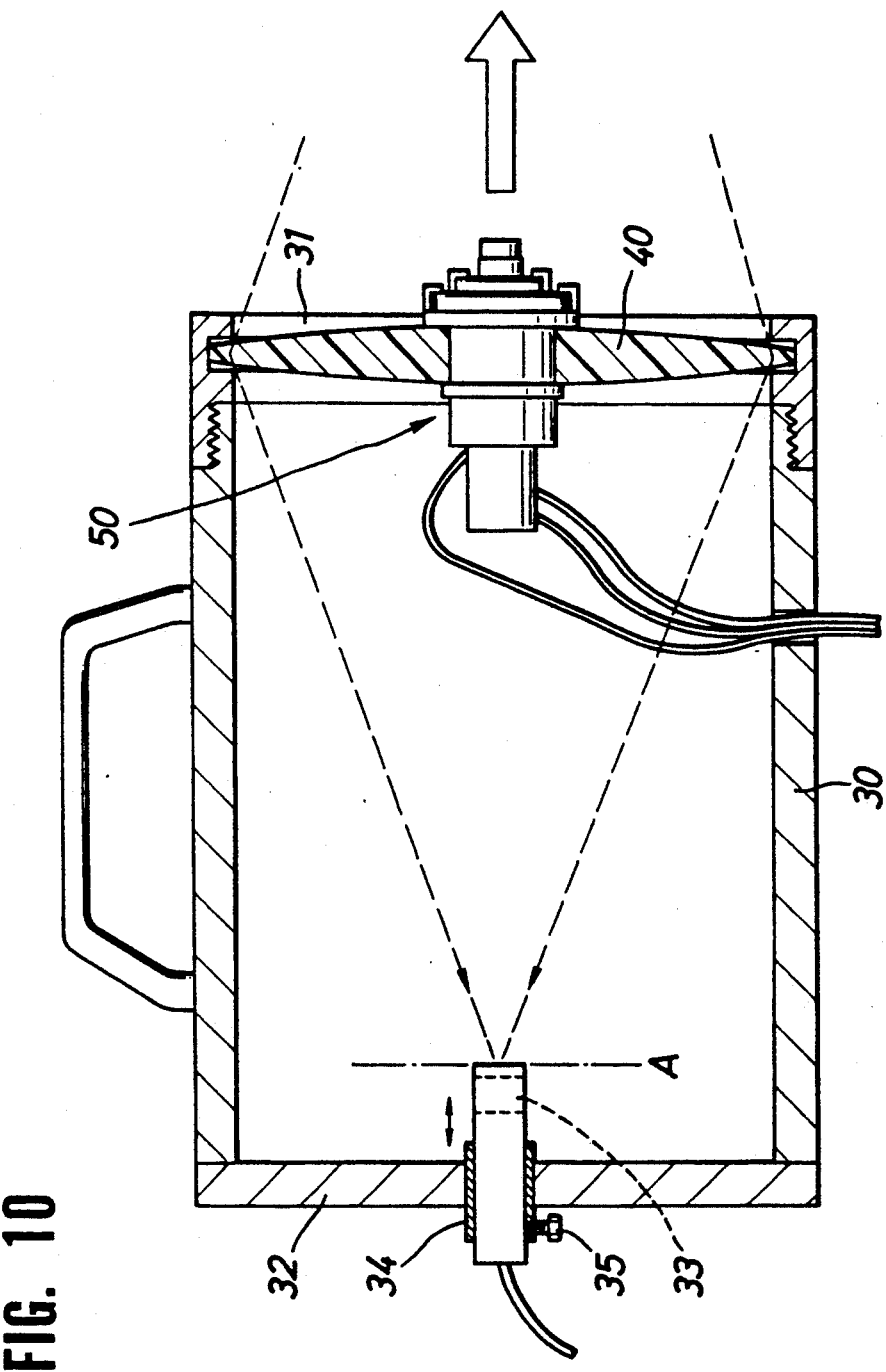
FIG. 10 is a section view of the laser transmitter-receiver unit of the gas detection device of the present invention.

FIG. 10 illustrates one embodiment of a portable laser transmitter-receiver unit for the gas detection device for detecting methane gas shown in FIG. 9.

In this gas detection device, a unit ring 31, in which is mounted a condensing lens 40 and a laser transmitter 50, is screwed onto the front end (the right end in the drawing) of a tubular casing 30, while a plate 32 is attached with screws to the rear end (the left end in the drawing) so that the inside of the casing is hermetically sealed. A sleeve 34 which houses a light detector 33 comprising a PIN photodiode or the like for detecting the intensity of a reflected laser beam is mounted at the center of the plate 32 in a manner allowing a freely advancing and retreating movement of the light detector 33 in the directions indicated by the arrows.

Figure 11:
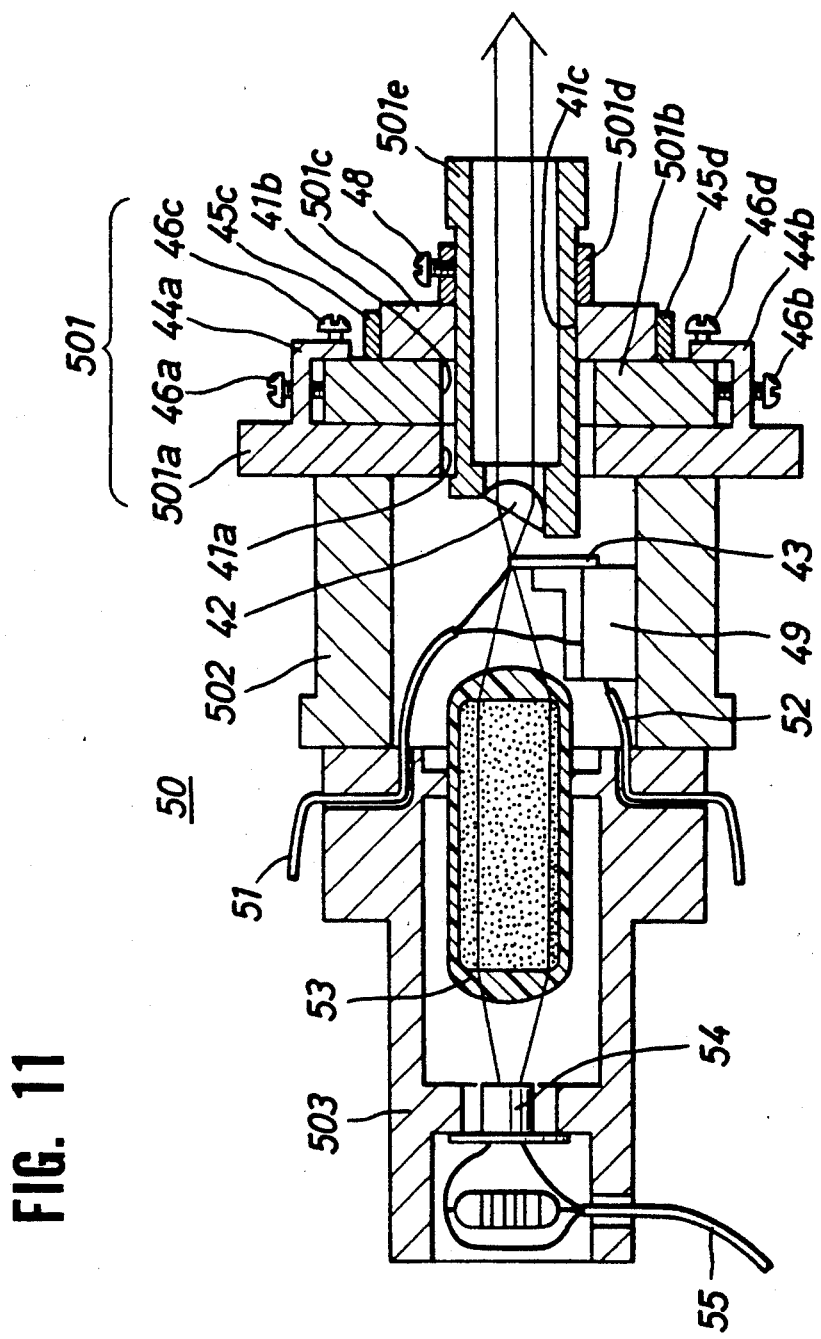
FIG. 11 is a section view of a laser transmitter used in the embodiment of the present invention shown in FIG. 10.
Figure 12:
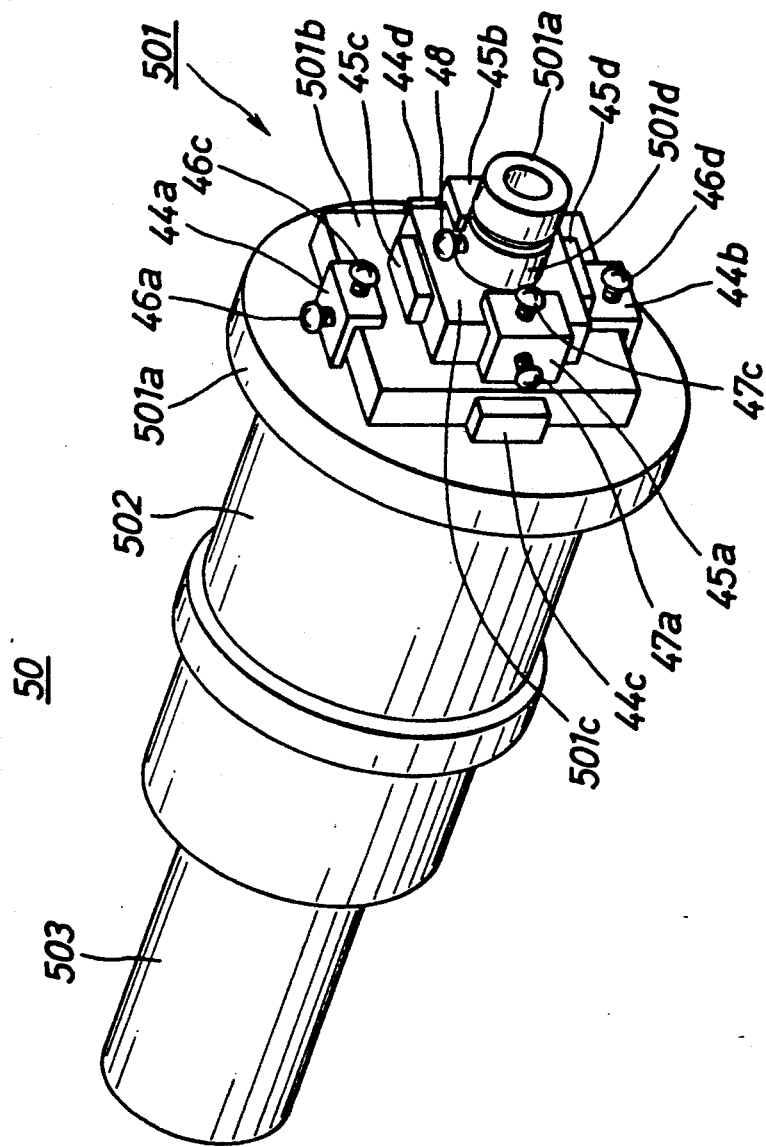
FIG. 12 is an external perspective view of the laser transmission module shown in FIG. 11.

Now referring to FIG. 11, the structure of the laser transmitter 50 will be explained. FIG. 12 is a perspective view of the laser transmitter shown in FIG. 11, viewed from the front.

The laser transmitter 50 comprises an optical axis adjustment block 501, an aluminum-walled tube 502, and a stepped aluminum sleeve 503, all of which are mounted and secured on a common centerline.

The optical axis adjustment block 501 comprises a circular plate 501a with a center opening 41a, which is secured to the sleeve 502; a rectangular y-axis adjusting plate 501b with a center opening 41b, which slideably contacts the plate 501a, for adjusting the optical axis in the y-axis direction (the vertical direction in the drawing); a rectangular x-axis adjusting plate 501c with a center opening 41c, which slideably contacts the y-axis adjusting plate 501b for adjusting the optical axis in the x-axis direction (the direction perpendicular to the paper in the drawing); and a ring 501d which contacts the x-axis adjusting plate 501c. The sleeve 501e penetrates and is enclosed by the center opening 41a in the plate 501a, the center opening 41b in the y-axis adjusting plate 501b, the center opening 41c in the x-axis adjusting plate 501c, and the ring 501d. A collimating lens 42 with a diameter of 5 mm, and a focal length of 4.6 mm, for converting the laser beam into parallel beams, is mounted in the inner end (the left end in the drawing) of the sleeve 501e, inclined at an angle of about 30°. In FIG. 11, the laser beam emitted from the semiconductor laser 43 is polarized in the direction perpendicular to the surface of the drawing, so that the collimating lens 42 can rotate 90° around the optical axis from the position shown in the drawing to reduce the reflection loss. The position of the collimating lens can also be adjusted vertically, laterally, and longitudinally.

A pair of opposing right-angled leaves 44a, 44b are formed close to the upper and lower peripheral edges, and a pair of guide leaves 44c, 44d are formed close to the left and right peripheral edges on the outer vertical surface of the circular plate 501a. A pair of opposing right-angled leaves 45a, 45b are formed on the left and right sides close to the peripheral edges on the outer vertical surface of the y-axis adjusting plate 501b. Also, as shown in FIG. 11, a pair of guide leaves 45c, 45d are formed close to the top and bottom peripheral edges on the outer vertical surface of the y-axis adjusting plate 501b. A pair of adjusting screws 46a, 46b for positional adjustment in the y-axis direction of the y-axis adjusting plate 501b, and a pair of set screws 46c, 46d for securing the y-axis adjusting plate 501b, penetrate tapped holes in the leaves 44a, 44b of the circular plate 501a. An adjusting screw 47a (see FIG. 12) for positional adjustment in the x-axis direction of the x-axis adjusting plate 501c, and a set screw 47c for securing the x-axis adjusting plate 501c penetrate tapped holes in the leaves 45a, 45b of the y-axis adjusting plate 501b.

In addition, a set screw 48 is provided in the ring 501d for securing the sleeve 501e after positional adjustment in the z-axis direction (the lateral direction in the drawing).

Next, the semiconductor laser 43 and a Peltier element 49 for controlling the temperature of the laser 43, thermally bonded into a unit through a copperplate block and an aluminum chip, are positioned on the bottom section of the inner surface of the sleeve 502. The thermal conduction time constant is about one second. A pair of external electrical lead wires 51, 52 are connected to the semiconductor laser 43 and the Peltier element 49.

A methane reference cell 53 is positioned inside the stepped sleeve 503. Methane gas at a partial pressure of 200 Torr and nitrogen gas are filled at a pressure of one atmosphere into the methane reference cell 53 pyrex tube 10 mm in diameter. Both ends of the pyrex tube play the roles of lenses. A light detector 54 for detecting the intensity of the laser beam passing through the methane reference cell 53 is positioned in the rear end of the sleeve 503. A lead wire 55 is connected to the beam detection device 54. The laser transmitter module 50 with this configuration is interposed in an opening at the center of the condensing lens 40 and secured by an adhesive.

The method of operating the methane gas detection device of FIG. 10 will next be explained.

Before the device is operated the optical axis and the focal point must be adjusted. To do this, the sleeve 34 is removed from its mounting on the plate 32 which forms the rear section of the cylindrical casing 300, and, in its place, a monitoring sleeve to which a semi-transparent tape is applied on the inside of the front end, is inserted without the beam detection apparatus into the center opening of the plate 32 to a suitable position.

First, the beam detection apparatus (2 cm effective diameter) is positioned about 5 meters in front of the gas detection apparatus, and the position of the beam detection apparatus is adjusted so that the optical image falls on the center of the semi-transparent tape applied to the front end of the sleeve 34.

Next, the laser beam emitted in the forward direction from the semiconductor laser 43 is converted to a parallel beam by the collimator lens 42 which passes through the sleeve 501e in the forward direction. The laser beam emitted in the rear direction from the semiconductor laser 43 passes through the methane reference cell 53 and its intensity is detected by the light detector 54 positioned at the rear.

The position of the collimator lens 42 is adjusted so that the forward projected laser beam strikes a detector placed about 5 meters forward. This adjustment is made in the following manner.

Specifically, while monitoring the output from the light detector positioned in front of the gas detection device with an oscilloscope or a voltmeter, the output is adjusted to a maximum by releasing the set screw 47c for the x-axis adjusting plate 501c, moving the x-axis adjusting plate 501c horizontally, specifically in the x-axis direction, by using the adjusting screw 47a then retightening the set screw 47c after the maximum position is reached. In the same manner, an adjustment is made for the y-axis adjusting plate 501b by releasing the set screws 46c, 46d, moving the y-axis adjusting plate 501b vertically, specifically in the y-axis direction, by using the adjusting screws 46a, 46b, then retightening the set screws 46c, 46d after the maximum position for the output of the light detector is reached. Adjustment in the longitudinal direction (the left-right direction in FIG. 11) is made by loosening the set screw 48, moving the sleeve 501e in the longitudinal direction until the output from the light detector is at a minimum, then retightening the set screw 48. This completes the optical axis adjustment.

At this point, the monitoring sleeve is removed from the plate 32 at the rear of the methane gas detection device, and the sleeve 34 on which is positioned the light detector 33 is reinserted to the same position and resecured to the plate 32 with a set screw 35. As a result, the laser beam reflecting from the target strikes the light detector 33. The operator observes the output from the light detector 33 using a separately-provided monitor, and slides the sleeve 34 in and out in the axial direction until the maximum output value is obtained. The set screw 35 is tightened at this maximum point. This completes the sensitivity adjustment operation. Because it is unnecessary to rigidly constrict the focal point of the reflected beam at the light detector 33, even if the distance to the target varies slightly, it is unnecessary to readjust the position of the light detector 33.

This completes the entire adjustment operation. To detect methane leaks, the laser beam is directed toward the probed area and hits the reflection target about five meters ahead of the gas detection device. The reflected laser light is collected and focused on the light detector 33. The output signal from the light detector 33 is fed into the two lock-in amplifiers 14 and 19. The signals from the two lock-in amplifiers are fed into the divider 20, which calculates the ratio R of the two signals. The methane concentration can be determined from R.

In the above-described embodiment of the present invention the focus adjustment was done by moving the light detector 33 manually. However, if the autofocus technology which is widely used in the camera industry and the like were utilized, it would be possible to make the focus adjustments automatically. The gas which is the object of the measurement is not restricted to methane gas. Other gases can, of course, be detected by the same principle.

As outlined in the foregoing explanation, in the present invention a semiconductor laser is used in which the wavelength and intensity vary with the drive current and the temperature. A laser beam can be generated whose wavelength and intensity are modulated at a special frequency by modulating the drive current. The device is constructed so that the laser beam passes through a probed atmosphere containing an unknown concentration of a gas whereby the concentration of the gas can be detected with high sensitivity and accuracy by the second harmonic signal or the fundamental frequency signal in the transmitted laser beam. In addition, accurate gas concentration measurement is possible regardless of the measurement environment by detecting the fundamental frequency component and the second harmonic component simultaneously and measuring the ratio between the two. Accordingly, the present invention can be effectively utilized in a portable unit for detecting gas leaks and the like in any type of atmosphere. Furthermore, it is also possible to utilize the present invention to selectively detect the concentration of a specific gas in an atmosphere which is a mixture of many gases.

The laser transmitter of the present invention comprises a collimator lens positioned on one side of a semiconductor laser for converting a laser beam into a parallel beam; a sealed reference gas cell, containing a gas to be detected, and a detector positioned on the opposite side of the semiconductor laser for detecting the intensity of the laser beam passing through the reference gas cell; and an optical axis adjusting means for adjusting the direction of the laser beam, with the collimator lens displaced in a plane at right angles to the optical axis. The gas detection device comprises the laser transmitter mounted in the center of the condensing lens, and a light detection means which detects the intensity of the reflected laser light condensed by the condensing lens. This simple design makes a small portable gas detection device possible.

What we claim is:

1. A gas detection device, aimable at a reflective surface, for detecting the presence of a predetermined gas between said detecting device and said reflective surface, said device comprising:

mounting means, having an axis;

laser means, disposed within said mounting means and along said axis, to project a coherent beam of light along said axis toward said reflective surface;

a convergent lens, having an optical axis, disposed within said mounting means, said optical axis substantially coincident with said mounting means axis;

a light detector disposed substantially at a focal point of said converging lens and responsive to said coherent beam reflected from said surface through said convergent lens;

means, responsive to the output of said light detector, for determining the presence of the gas to be detected, wherein said means for determining the presence of the gas to be detected comprises:

means for establishing a central wavelength of said coherent beam of light, said central wavelength being at a predetermined spectral line of said gas to be detected;

means for modulating the wavelength of said coherent beam of light about said central wavelength at a predetermined modulation frequency;

a first lock in amplifier, responsive to the fundamental frequency of said detected output;

a second lock in amplifier, responsive to the second harmonic frequency of said detected output;

a divider, coupled to the first lock in amplifier and second lock in amplifier, providing a signal proportional to the ratio of the fundamental and second harmonic frequencies of said beam; and means, responsive to said divider, for determining the presence of the gas to be detected in said sample.

* * * * *